US008722115B2

(12) United States Patent
Heaton et al.

(10) Patent No.: US 8,722,115 B2
(45) Date of Patent: *May 13, 2014

(54) METHODS FOR IMPROVING HEALTH IN ANIMALS

(71) Applicant: Quality IP Holdings, Inc., Cason City, NV (US)

(72) Inventors: Amy L. Heaton, Salt Lake City, UT (US); Mitchell K. Friedlander, Salt Lake City, UT (US); Dennis Gay, Salt Lake City, UT (US)

(73) Assignee: Quality IP Holdings, LLC, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/623,113

(22) Filed: Sep. 20, 2012

(65) Prior Publication Data

US 2014/0079827 A1    Mar. 20, 2014

(51) Int. Cl.
*A61K 36/55* (2006.01)
*A61K 36/00* (2006.01)
*A61K 47/00* (2006.01)
*A61K 9/14* (2006.01)
*A61K 9/00* (2006.01)

(52) U.S. Cl.
USPC ........... 424/745; 424/725; 424/774; 424/439; 424/489; 424/400

(58) Field of Classification Search
None
See application file for complete search history.

(56) References Cited

PUBLICATIONS

Fung et al. (2002) J. Clin. Pharmacol. 42: 30-36.*
Website document entitled "Growth Hormone: Amino Acids as GH Secretagogues" (available at http://www.vrp.com/amino-acids/growth-hormone-amino acids-as-gh-secretagogues-a-review-of-theliterature?utm_source=RSStwitterfeed&utm_medium=twitter). Dowloaded from website Apr. 8, 2013.*
Alba-Roth et al.; Arginine Stimulates Growth Hormone Secretion by Suppressing Endogenous Somatostatin Secretion; Journal of Clinical Endocrinology and Metabolism, vol. 67, No. 6, 1988; 1186-1189.
Albert et al.; Low-Dose Recombinant Human Growth Hormone as Adjuvant Therapy of Lifestyle Modifications in the Management of Obesity; Journal of Clinical Endocrinology & Metabolism 89(2) 695-704; 2004.
Bernardi et al.; Somatotropic axis and body weight in premenopausal and post-menopausal women: evidence fora neuroendocrine derangement, in absence of changes of insulin-like growth factor binding protein concentrations; Human Reproduction vol. 12, No. 2 pp. 279-287, 1998.
Bidlingmaier et al.; Growth Hormone; Handbook of Experimental Pharmacology 195; 2010; pp. 187-200.
Bjorntorp, et al.; Hypothalamic Origin of the Metabolic Syndrome X; Annals New York Academy of Sciences, pp. 297-307; 1999.
Bjorntorp, P.; Do Stress reactions cause abdominal obesity and comorbidities?; The International Association for the Study of Obesity, Obesity reviews; 2 73-85; 2001.
Bjorntorp, P.; The regulation of adipose tissue distribution in humans; International Journal of Obesity (1996) 20, 191-302.
Blackman et al.; Growth Hormone and Sex Steroid Administration in Healthy Aged Women and Men A Randomized Controlled Trial; JAMA, Nov. 12, 2002—vol. 288, No. 18; pp. 2282-2292.
Bredella, et al.; Peak Growth Hormone-Releasing Hormone-Arginine-Stimulated Growth Hormone iS Inversely Associated with Intramyocellular and Intrahepatic Lipid Contentin Premenopausal Women with Obesity; J. Clin Endrocrinol Metab. Oct. 2009; 94(10): 3995-4002.
Carli et al.; Changes in the exercise-induced hormone response to branched chain amino acid administration; Eru. J. Apl. Physiology (1992) 64:272-277.
Chromiak et al.; Use of Amino Acids as Growth Hormone-Releasing Agents by Athletes; Nutrition 18:657-661, 2002.
Corpas et al.; Human Growth Hormone and Human Aging; Endocrine Reviews, vol. 14, No. 1; 1993; pp. 20-39.
Corpas et al.; Oral Arginine-Lysine Does not Increase Growth Hormone or Insulin-like Growth Factor-I in Old Men; Journal of Gerontology: 1993, vol. 48, No. 4, M128-M133.
Ding et al.; Novel serum protein biomarkers indicative of growth hormone doping in healthy human subjects; Preteomics 2011, 11, 3565-3571.
Fogelholm et al. Low-Dose Amino Acid Supplementation: No Effects on Serum Human Growth Hormone and Insulin in Male Weightlifters; International Journal of Sport Nutrition, 1993, 3, 290-297.
Gourmelen et al., Effet du chlorhydrate d'ornithine sur le taux plamatique de l'hormone de croissane (HGH); Annels D'Endocrinologie; pp. 526-528; 1972.
Hayes et al.; Recombinant Human Growth Hormone and Recombinant Human Insulin-Like Growth Factor I Diminish the Cataboloic Effects of Hypogonadism in Man: Metabolic and Molecular Effects; The Journabf of Clinical Endocrinology & Metabolism; vol. 86, No. 5; 2001.
Hersch et al.; Growth hormone (GH)-releasing hormone and GH secretagogues in normal aging: Fountain of Youth or Pool of Tantalus?; Clinical Interventions in Aging 2008:3(1) 121-129.

(Continued)

*Primary Examiner* — Chris R Tate
*Assistant Examiner* — Russell Fiebig
(74) *Attorney, Agent, or Firm* — TraskBritt, P.C.

(57) ABSTRACT

A method of improving health in an animal includes administering to the animal a nutritional supplement comprising an amino acid secretagogue composition, which stimulates the pituitary gland in the animal to produce growth hormone. The nutritional supplement may be administered orally. The nutritional supplement may comprise L-arginine hydrochloride, L-pyroglutamic acid, L-lysine hydrochloride, and cysteine. When desired, the nutritional supplement may consist essentially of L-arginine hydrochloride, L-pyroglutamic acid, L-lysine hydrochloride, N-acetyl-L-cysteine, L-glutamine, and schizonepeta powder.

15 Claims, No Drawings

(56) References Cited

PUBLICATIONS

Iranmanesh et al., Age and Relative Adiposity are Specific Negative Determinants of the Frequency and Amplitude of Growth Hormone (GH) Secretory Bursts and the Half-Life of Endogenous GH in Healthy Men; Journal of Clinical Endocrinology and Metabolism; vol. 73, No. 5; pp. 1081-1088, 1991.

Isidori et al.; A Study of growth hormone release in man after oral administration of amino acids; Current Medical Research and Opinion; vol. 7, No. 7, 1981; pp. 475-481.

Karlsson et al.; Effects of growth hormone treatment on he leptin system and on energy expenditure in abdominally obese men; European Journal of Endocrinology (1998) 138 408-414.

Kraemer et al.; Chronic Resistance training in women potentiates growth hormone in vivo bioactivity: characterization of molecular mass variants; Am. J. Physiol Endocrinol Metab 291: E1177-E1187, 2006.

Lambert et al.; Failure of Commercial Oral Amino Acid Supplements to Increase Serum Growth Hormone Concentrations in Male Body-Builders; International Journal of Sport Nutrition, 1993, 3, 298-305.

Legakis et al.; Human Galanin Secretion is Increased Upon Normal Exercise Test in Middle-Age Individuals; Endocrine Research 26(3), 357-365 (2000).

Maccario et al.; Relationships between IFG-I and age, gender, body mass, fat distribution, metabolic and hormonal variables in obese patients; International Journal of Obesity (1999) 23, 612-618.

Makimura et al.; The relationship between reduced testosterone, Stimulated growth hormone secretion and increased carotid inima-media thickness in obese men; Clin Endocrinol (Oxf). Nov. 2010; 73(5): 622-629.

Menagh et al.; Growth Hormone Regulates the Balance Between Bone Formation and Bone Marrow Adiposity; JBMR; vol. 25, No. 4, Apr. 2010, pp. 757-768.

Merimee et al.; Arginine-Initiated Release of Human Growth Hormone; The New England Journal of Medicine; Jun. 26, 1969; pp. 1434-1438.

Nindl et al.; Growth hormone pulsatility profile characteristics following acute heavy resistance exercise; J. Appl Physiol 91: 163-172, 2001.

O'Connor et al.; Interrelationships of Spontaneous Growth Hormone Axis Activity, Body Fat, and Serum Lipids in Healthy Elderly Women and Men; Metabolism, vol. 48, No. 11 Nov. 1999: pp. 1424-1431.

Papadakis et al.; Effect of growth hormone replacement on wound healing in healthy older men; Would Repair and Regeneration Oct.-Dec. 1996; pp. 421-425.

Papadakis et al.; Growth Hormone Replacement in Healthy Older Men Improves Body Composition but Not Functional Ability; Ann Intern Med. 1996; 124-: 708-716.

Pasquali et al.; Hormones and pathophysiology of obesity; Hormones and Obesity; 2001 pp. 9-20.

Pelsers et al.; Influence of Gender in Growth Hormone Status in Adults: Role of Urinary Growth Hormone; Clinical Chemistry 45, No. 3, 1999, pp. 443-444.

Perry, Horace M. III; The Endocrinology of Aging; Clinical Chemistry 45:8(B); 1369-1376 (1999).

Rubin et al.; New anabolic therapies in osteoporosis; Current Opinon in Reeumatology 2002, 14:433-440.

Rudman et al.; Effects of Human Growth Hormone in Men over 60 Years Old; The New England Journal of Medicine; vol. 323, Jul. 5, 1990; 6 pages.

Su et al.; Insulin-like growth factor 1 and hair growth; 1999 Dermatology Online Journal; 20 pages.

Suminski et al.; Acute Effect of Amino Acid Ingestion and Resistance Exercise on Plasma Growth Hormone Concentration in Young Men; International Journalof Sport Nutrition, 1997, 7, 48-60.

Twickler et al.; Adult-Onset Growth Hormone Deficiency: Relation of Postprandial Dyslipidemia to Premature Atherosclerosis; The Journal of Clinical Endocrinology & Metabolism 88(6): 2479-2488, 2002.

Vance, Mary L.; Growth Hormone for the Elderly?; The New England Journal of Medicine; Jul. 5, 1990; pp. 52-54.

White et al.; Effects of an Oral Growth Hormone Secretagogue in Older Adults; J. Clin Endocrin Metab.; 2009; 29 pages.

Zouboulis et al.; Intrinsische Hautalterung; Eine kritische Bewertung der Rolle der Hormone; Hautarzt 2003 54: 825-832.

\* cited by examiner

METHODS FOR IMPROVING HEALTH IN ANIMALS

TECHNICAL FIELD

Embodiments of the present disclosure generally relate to methods and nutritional supplements for improving health in animals.

BACKGROUND

Growth hormone is an anabolic hormone capable of promoting linear growth, weight gain and whole body nitrogen retention in animals. Growth hormone is produced in somatotroph cells of the anterior pituitary gland of animals and secreted throughout life. It is mainly controlled in the brain by two hypothalamic peptides: growth hormone releasing hormone (GHRH), which stimulates its secretion and synthesis; and somatostatin, which inhibits them. Growth hormone is known to promote skeletal growth, to increase nitrogen retention and protein synthesis, and to affect glucose and lipid metabolism in animals.

As animal grows older, the growth hormone undergoes considerable decrement resulting in a loss of skeletal muscle mass, osteoporosis, increased fat deposition and decreased lean body mass. It has been demonstrated that the development of these changes can be offset by recombinant growth hormone therapy. However, current recombinant growth hormone therapy has several shortcomings including frequent subcutaneous or intravenous injections, insulin resistance and impaired glucose tolerance.

Growth hormone has been administered to animals to offset the growth hormone deficiency in aged animals. Furthermore, there are reports of using growth hormone to boost certain desirable performances of animals. For example, growth hormone has been used to enhance growth performance in animals by increasing lean body mass with an overall improvement in feed efficiency, and to enhance fertility in animals. Additionally, growth hormone has been used to stimulate milk production and achieve an enhanced milk yield in mammals.

U.S. Pat. No. 4,521,409, issued on Jun. 4, 1985 to Bauman, and U.S. Pat. No. 5,004,728, issued on Apr. 2, 1991 to Chalupa disclose the administration of growth hormone to cattle and ruminants to stimulate milk production with an increase in feed to milk conversion. In U.S. Pat. No. 5,416,073, issued on May 16, 1995 to Coy, growth hormone is used to increase milk production in dairy cows and to increase growth rates in animals such as cattle, sheep, and swine.

U.S. Pat. No. 5,008,244, issued on Apr. 16, 1991 to Miller discloses an administration of growth hormone to food-producing animals to increase their fertility by improving embryonic survival and litter size during the reproductive stage of growth. In U.S. Pat. No. 5,583,106, issued on Dec. 10, 1996 to Stanisiewski, an enhanced reproductive performance in cattle is achieved by commencing administration of growth hormone during the early postpartum period.

U.S. Pat. No. 5,637,566, issued on Jun. 10, 1997 to Walker et al. describes the use of growth hormone to improve carcass quality and/or food conversion efficiency in animals. In U.S. Pat. No. 4,792,546, issued on Dec. 20, 1988 to Baker, growth hormone is administered to food-producing animals to increase weight gain and at the same time reduce fat deposition and improve the lean meat to fat ratio.

SUMMARY OF THE DISCLOSURE

The present disclosure includes a nutritional supplement and a method of using the same for improving health in animals. The nutritional supplement is an amino acid secretagogue composition, which stimulates the pituitary gland of animals to release growth hormone.

A particular embodiment of the present disclosure relates to a nutritional supplement for improving health in animals, the nutritional supplement comprising L-arginine, L-pyroglutamic acid, L-lysine, and cysteine.

Another particular embodiment relates to a nutritional supplement for improving health in animals, the nutritional supplement consisting essentially of L-arginine hydrochloride, L-pyroglutamic acid, L-lysine hydrochloride, N-acetyl-L-cysteine, L-glutamine and schizonepeta powder.

Other embodiments are drawn to methods of increasing growth hormone in animals, the methods including administering the disclosed nutritional supplement to an animal. In particular embodiments, the method includes orally administering the disclosed nutritional supplement to an animal.

DETAILED DESCRIPTION OF THE DISCLOSURE

The present disclosure relates to methods and nutritional supplements for improving health in animals. The nutritional supplement is an amino acid secretagogue composition, which stimulates the pituitary gland in an animal to produce growth hormone. Increased production of growth hormone in animals may prevent the loss of skeletal muscle mass, osteoporosis, increased fat deposition, decreased lean body mass, and other disorders. The supplement of the present disclosure may work as a dietary supplement by assisting the animal's ability to secrete growth hormone naturally in a manner which is safe and effective.

As used herein, the term "animal" means any species of the kingdom Animalia, including mammals, avians, reptiles or amphibians. It may include a food-producing animal (e.g., chicken, turkeys, ducks, geese, guinea henspig, cattle, lambs, fish, etc.); a pet such as dog and cat; or a working animal such as horse.

As used herein, the term "mammal" means a warm blooded vertebrate, including non-human animals such as murine, porcine, canine and feline. It may include ungulates or hooved animals (e.g., cattle, goats, pigs, horse, sheep, etc.); rodents (e.g., guinea pigs, hamsters, mice, rats, etc.); lagomorphs such as rabbits; primates (e.g., monkeys, baboons, humans, etc.); or the like. By way of non-limiting examples, mammal may include cattle, sheep, goat, or swine.

A particular embodiment of the present disclosure relates to a nutritional supplement for improving health of animals, the nutritional supplement including L-lysine, L-arginine, oxo-proline, and at least one of cysteine and glutamine. The supplement may additionally include both cysteine and glutamine and/or schizonepeta powder. In particular embodiments, a functional dosage may include L-arginine at a level between 0.1-6 mmol, oxo-proline at a level between 0.1-8 mmol, and/or the L-lysine in an amount between 0.1-12 mmol. The cysteine and/or glutamine may be contained at a level between 0.001-6 mmol. The cysteine may be n-acetyl L-cysteine, and the glutamine may be L-glutamine. The amino acids may be delivered as non-toxic salts thereof, effective complexes thereof, stable chelates thereof, active esters thereof, functional derivatives thereof, or mixtures thereof, which are effective to increase growth hormone levels in animals. The nutritional supplement may be present in an amount of 2.9 grams. Dosages are generally calculated in the range of about 20-50 gms per kg of body weight of the animal. The nutritional supplement may be administered to animals orally. The supplement may be in any acceptable and known oral formulation including, but are not limited to, powder, tablet, capsule, or liquid form.

Another particular embodiment relates to a nutritional supplement for improving health of animals, the nutritional supplement consisting essentially of L-lysine HCl, L-arginine HCl, oxo-proline, N-acetyl L-cysteine, L-glutamine, and schizonepeta (aerial parts) powder. In particular embodiments, a functional dosage may include L-arginine HCl at a level between 0.1-6 mmol, and oxo-proline at a level between 0.1-8 mmol, and/or the L-lysine HCl in an amount between 0.1-12 mmol. The n-acetyl L-cysteine and/or L-glutamine may be contained at a level between 0.001-6 mmol. In another particular embodiment, a functional dosage may include L-arginine HCl at a level between 2.5-4.5 mmol, oxo-proline between 4-6 mmol, and/or the L-lysine HCl in an amount between 7-9 mmol. The n-acetyl L-cysteine and/or L-glutamine may be contained at a level between 0.001-0.5 mmol. The nutritional supplement may be administered to animals orally. The supplement may be in any acceptable and known oral formulation including, but are not limited to, powder, tablet, capsule, or liquid form.

Other embodiments are drawn to methods of increasing growth hormone in animals, the methods including administering the disclosed nutritional supplement to an animal. In particular embodiments, the method includes orally administering the disclosed nutritional supplement to an animal. The amount of dosage and frequency of administration may be varied according to many factors including, but are not limited to, animal species, ages and health.

The disclosed nutritional supplements may be administered to an animal to improve health, including by: increasing growth performance; enhancing lean body mass with an overall improvement in feed efficiency; improving reproductively performance; stimulating milk production; boosting milk yield; or combinations thereof.

In accordance with the "consist essentially of" and "consisting essentially of" language, the nutritional supplement is essentially limited to the aforementioned ingredients and does not include any additional active ingredients intended to add nutritional content (e.g., vitamins, minerals, etc.), but may include additional ingredients not intended to add nutritional content such as ingredients intended to fulfill a non-nutritional purpose (e.g., coloring, fillers, flavoring, an ingredient for maintaining the structural form, etc.).

Each ingredient of the nutritional supplement may be prepared in accordance with any method known to one of ordinary skill in the art. Alternatively, each ingredient may be obtained in a fully prepared from a commercially available source.

The nutritional supplement may be in any suitable oral administration form, including but not limited to: a chewable form, a liquid form, a spray form, a capsule form, a suppository form, dissolvable wafer, and a powder form.

Irrespective of the structural form of the nutritional supplement, the ingredients of the nutritional supplement may be distributed homogeneously or non-homogeneously within the nutritional supplement.

The nutritional supplement may be administered to an animal on a regular basis, such as a weekly or monthly intake at a dosage tailored to the animal's needs; i.e., the nutritional supplement may be administered regularly as multiples (1×, 2×, etc.) of the structural units (pills, tablets, capsules, etc.) in accordance with the needs of the animal. For example, an elderly animal is likely to need higher daily doses than does a young animal. Alternatively, the nutritional supplement may be administered on an as-needed basis at a dosage tailored to the animal's needs, such as administering the nutritional supplement to cattle during the early postpartum period to enhance reproductively performance. Veterinarian counseling may be beneficial for arriving at a desirable or optimal dosage tailored to the animal's needs.

The combination of types of amino acids, mass ranges, and specific formulations may be selected to be synergistically balanced and of adequate quantity to achieve the desired physiological effect, namely, growth hormone release. Improper combinations of the amino acids may be ineffective. The component amino acids are synergistic in the sense that several of them when combined together, synergistically stimulate the release of human growth hormone. The combination may also be chosen to reduce or inhibit chemical combination or reaction between the amino acids.

EXAMPLES

Example 1

The short-term effects of the disclosed supplement on the growth hormone level in animals are tested two hours after administration. The animal subjects are administered the capsules of supplement (SeroVital™) or an identical looking placebo. SeroVital™ is a blend of l-lysine HCl, l-arginine HCL, oxo-proline, N-acetyl-l-cysteine, l-glutamine, and schizonepeta (aerial parts) powder. Animal subjects are administered approximately 35 gms per kg of body weight. Blood is drawn at 15, 30, 60 and 90 and 120 minutes for assay. The growth hormone level is measured at each time point using the Siemens Immulite 2000 (intra-assay CV was 3.72%, inter-assay CV was 5.70%, and the detection limit for GH was 0.05 ng/ml). The 15 and 120 minute time points are additionally assayed for triiodothyronine (T3) as informative for mechanistic investigations.

The mean growth hormone in the animal subjects are increased more than 600% after the administration of supplement from 0.17 at baseline to 1.33 ng/ml at 120 minutes, while there is are no increases observed in the mean growth hormone of the animal subjects after the administration of placebo.

The growth hormone levels from baseline to 120 minutes (the growth hormone level at 120 minutes minus the growth hormone level at 0 minute), are increased about two fold when compared to the administration of a placebo. Overall, 120 minutes after the administration of the supplement, the growth hormone levels are significantly higher in absolute levels or by AUC.

Furthermore, the animals that were administered SeroVital™ will exhibit a deceased reduction in T3 by nearly one-half over the same time period, compared to the animals administered with the placebo. These results affirm that somatostatin inhibition plays a mechanistic role in the ability of SeroVital™ to induce significant increases in serum growth hormone levels in animal subjects.

These findings demonstrate that a specialized low-dose amino acid supplement can significantly increase short-term growth hormone levels in animals.

Example 2

The effect of the nutritional supplement on endurance and fat metabolism in animals are investigated. Each animal subject is measured for baseline weight, height, body fat percent and resting metabolic rate. Then, each animal subject is administered with the supplement SeroVital™, which is a blend of l-lysine HCl, l-arginine HCl, oxo-proline, N-acetyl-l-cysteine, l-glutamine, and schizonepeta (aerial parts) powder for 2 weeks before being measured again for weight, height, body fat percent and resting metabolic rate. The measurements before and after the administration of the supplement are analyzed.

Mean $VO_{2max}$ of the animal subjects increases compared to baseline. After the period of supplementation with SeroVital™, the mean RMR increases compared to baseline (P=0.165). Estimated daily calorie expenditure also increases.

After two weeks of supplementation with the supplement SeroVital™, both RMR and estimated daily calorie expenditure of the animal subjects tend to increase, evidencing the potential of the supplement to impart long-term fat burning effects. Additionally, endurance as measured by $VO_{2max}$ in the post-absorptive state significantly improves. Overall, the animal subjects administered with the SeroVital™ supplement will show enhanced parameters of endurance, energy, and vitality.

Example 3

The effect of the nutritional supplement on lean body mass and weight change of animals is studied. The animal subjects in the first group are given daily doses of the nutritional supplement for 6 months at different dosing concentrations of active ingredients, while the animal subjects in the second group are given placebo. Weight, percent lean body mass, and percent fat body mass are chosen as primary measures of body composition at the 6 month analysis period. The weight, body composition, and physical performance (including endurance) of the animal subjects are determined before and after the treatment, along with hormonal data analysis.

The animal subjects treated with the nutritional supplement show a sustained increase in lean body mass and an improved physical performance.

While embodiments of the present invention have been described herein for purposes of illustration, many modifications and changes will become apparent to those skilled in the art. Accordingly, the appended claims are intended to encompass all such modifications and changes as fall within the true spirit and scope of this invention.

We claim:

1. A method of increasing growth hormone in a nonhuman mammal in need thereof, comprising:
   administering an effective amount of a nutritional supplement, consisting essentially of:
   about 1 mmol L-arginine;
   about 1 mmol Oxo-proline;
   about 2 mmol L-lysine;
   about 1.5 µmol N-acetyl L-cysteine;
   about 2 µmol L-glutamine; and
   about 125 µg Schizonepta (aerial parts) powder.

2. The method of claim 1, wherein administering the nutritional supplement comprises orally administering.

3. The method of claim 1, wherein administering the nutritional supplement comprises administering about 20-50 gms/kg of body weight of the nutritional supplement.

4. The method of claim 1, wherein the nutritional supplement is in powder, tablet, capsule, liquid, or wafer form.

5. The method of claim 1, wherein the nutritional supplement is administered once a week or once a month.

6. The method of claim 1, wherein the nutritional supplement is administered for at least one of following in the nonhuman mammal: increasing growth performance, enhancing lean body mass, improving reproductively performance, stimulating milk production, boosting milk yield, and increasing a feed efficiency.

7. A method of increasing growth hormone in a nonhuman mammal in need thereof, comprising:
   administering an effective amount of a nutritional supplement, consisting essentially of:
   3.44 mmol L-arginine;
   5.30 mmol Oxo-proline;
   8.21 mmol L-lysine;
   6.13 µmol N-acetyl L-cysteine;
   6.84 µmol L-glutamine; and
   0.50 mg Schizonepta (aerial parts) powder.

8. The method of claim 7, wherein the nutritional supplement consists of 725.50 mg L-arginine HCl; 683.70 mg L-pyroglutamic acid; 1499.30 mg L-lysine HCl; 1.00 mg N-acetyl L-cysteine USP; 1.00 mg L-glutamine; and 0.50 mg Schizonepta (aerial parts) powder.

9. The method of claim 7, wherein administering the nutritional supplement comprises orally administering the nutritional supplement.

10. The method of claim 7, wherein administering the nutritional supplement comprises administering about 20-50 gms/kg of body weight of the nutritional supplement.

11. The method of claim 7, wherein the nutritional supplement is in powder, tablet, capsule, liquid, or wafer form.

12. The method of claim 7, wherein the nutritional supplement is administered once a week or once a month.

13. The method of claim 7, wherein the nutritional is administered one to three times daily.

14. The method of claim 7, wherein the nutritional supplement is administered on an empty stomach.

15. The method of claim 7, wherein the nutritional supplement is administered for at least one of following in the nonhuman: increasing growth performance, enhancing lean body mass, improving reproductively performance, stimulating milk production, boosting milk yield, and increasing a feed efficiency.

* * * * *